(12) United States Patent
Gubbi Lakshminarasimha et al.

(10) Patent No.: US 10,524,697 B2
(45) Date of Patent: Jan. 7, 2020

(54) SYSTEM AND METHOD FOR MONITORING MOTOR RECOVERY IN A POST ACUTE STROKE TREATMENT

(71) Applicant: NEUROANALYTICS PTY. LTD., Brighton (AU)

(72) Inventors: Jayavardhana Rama Gubbi Lakshminarasimha, Bangalore (IN); Marimuthu Palaniswami, Kew (AU)

(73) Assignee: NEUROANALYTICS PTY. LTD., Brighton, Vic (AU)

( * ) Notice: Subject to any disclaimer, the term of this patent is extended or adjusted under 35 U.S.C. 154(b) by 329 days.

(21) Appl. No.: 15/505,003

(22) PCT Filed: Dec. 1, 2015

(86) PCT No.: PCT/AU2015/000725
§ 371 (c)(1),
(2) Date: Feb. 17, 2017

(87) PCT Pub. No.: WO2017/091843
PCT Pub. Date: Jun. 8, 2017

(65) Prior Publication Data
US 2017/0273600 A1   Sep. 28, 2017

(51) Int. Cl.
*A61B 5/00* (2006.01)
*A61B 5/11* (2006.01)

(52) U.S. Cl.
CPC .............. *A61B 5/11* (2013.01); *A61B 5/0022* (2013.01); *A61B 5/4848* (2013.01); *A61B 2562/0219* (2013.01)

(58) Field of Classification Search
CPC ........ A61B 5/11; A61B 5/1118; A61B 5/1124; A61B 5/0022; A61B 5/4842; A61B 5/4848
See application file for complete search history.

(56) References Cited

U.S. PATENT DOCUMENTS

| | | | |
|---|---|---|---|
| 8,750,971 B2 * | 6/2014 | Tran ..................... | A61B 5/0006 600/509 |
| 9,186,095 B2 * | 11/2015 | Machado ............. | A61B 5/6897 |
| 9,597,015 B2 * | 3/2017 | McNames ............ | A61B 5/1071 |
| 9,662,502 B2 * | 5/2017 | Giuffrida ............ | A61N 1/36067 |
| 2004/0044273 A1 * | 3/2004 | Keith ..................... | A61B 5/224 600/300 |

OTHER PUBLICATIONS

Gubbi et al., "Motor recovery monitoring using acceleration measurements in post acute stroke patients", Biomedical Engineering ONline, 2013 (Year: 2013).*
Heron et al. "Wireless acclerometry is feasible in acute monitoring of upper limb motor recovery after ischemic stroke", Cerebrovascular Diseases, 2014 (Year: 2014).*

* cited by examiner

*Primary Examiner* — Max F Hindenburg
(74) *Attorney, Agent, or Firm* — Symbus Law Group, LLC; Clifford D. Hyra

(57) ABSTRACT

System and method for monitoring motor recovery in a post-stroke treatment is disclosed. Motor activity data corresponding to limbs movement is collected during an acute stroke period. The motor activity data is transmitted to at least one base station and an activity value for each arm of two arms is calculated in a predefined time window by using the motor activity data. The activity value for each arm is compared thus providing the monitoring of the motor activity.

15 Claims, 11 Drawing Sheets

US 10,524,697 B2

SYSTEM AND METHOD FOR MONITORING MOTOR RECOVERY IN A POST ACUTE STROKE TREATMENT

CROSS-REFERENCE TO RELATED APPLICATIONS AND PRIORITY

The present application does not claim priority from any Patent Application.

TECHNICAL FIELD

The present disclosure in general relates to data monitoring. More particularly, the present disclosure relates to motor recovery monitoring in a post-acute stroke treatment.

BACKGROUND

Health monitoring has become a necessity as a result of increasing health awareness. In post-stroke cases, body movement monitoring may help in checking a pace of recovery. In case of acute strokes, round the clock monitoring is needed while delivering clot-busting medication.

Monitoring of motor recovery by clinical observation may be critical in providing a proper management of stroke patients. Such manual monitoring by experts may be time consuming and prone to errors. While relying on manual monitoring, there might be a case when patients who do not show early motor recovery and requiring urgent re-investigation, may get unnoticed.

Health monitoring may be done by using various health monitoring devices readily available in market. However, such health monitoring device may involve complexity in use and utmost care might be needed to handle them.

SUMMARY OF THE INVENTION

This summary is provided to introduce aspects related to system(s) and method(s) for monitoring motor recovery in a post-acute stroke treatment and the aspects are further described below in the detailed description. This summary is not intended to identify essential features of the claimed subject matter nor is it intended for use in determining or limiting the scope of the claimed subject matter.

The present disclosure relates to a system for monitoring motor recovery in a post-acute stroke treatment. The system comprises at least one sensor, for collecting a motor activity data corresponding to limb movement of a patient. The motor activity data is collected at an acute stroke period. The system further comprises a processor communicatively coupled to the at least one sensor and a memory coupled to the processor. The memory stores a plurality of modules to be executed by the processor and the plurality of modules are configured to transmit the motor activity data to at least one base station and the at least one base station comprises a transceiver for receiving the motor activity data and a processor with a memory. The memory stores a plurality of modules to be executed by the processor, and wherein the plurality of modules are configured to calculate an activity value for two arms from the data corresponding to the limb movement, by using the motor activity data in a predefined time window and compare the activity value between the two arms for monitoring the motor activity of the patient.

The present disclosure also relates to a method for providing motor recovery monitoring in a post-acute stroke treatment. The method comprises collecting, by at least one sensor, a motor activity data corresponding to limbs of a patient. The motor activity data is collected at an acute stroke period. The method further comprises transmitting, by the at least one sensor, the motor activity data to at least one base station, calculating, by a processor, an activity value for at least two arms from the limbs, by using the motor activity data in a predefined time window and comparing, by the processor, the activity value between the at least two arms for monitoring the motor activity of the patient.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

While aspects of described system and method device monitoring motor recovery in a post-acute treatment may be implemented in any number of different computing systems, environments, and/or configurations, the embodiments are described in the context of the following exemplary system.

Figure 1:
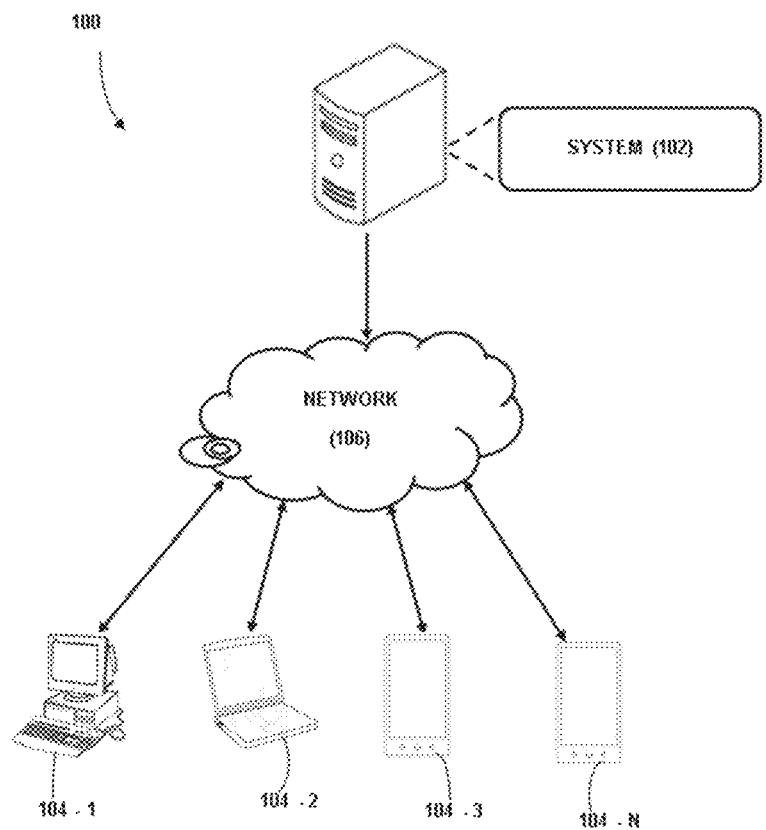
FIG. 1 illustrates a network implementation of a system monitoring motor activity in a post-acute stroke treatment, in accordance with an embodiment of the present subject matter.

Referring now to FIG. 1, a network implementation of the system 10o monitoring motor recovery in a post stroke treatment is disclosed. One or more sensor collects motor activity data corresponding to limb movement (also referred the limb movement data) of patient after the stroke. Once the patient is affected by stroke, he is taken to the hospital. In the hospital, as soon as the diagnosis is confirmed as stroke, the first line of treatment is injecting thrombolytic drugs. The first 24 hours after starting the treatment is critical to patient recovery. Normally, it will be clear within this 24 hours, whether an aggressive treatment is required. This time period is referred to as acute stroke period. The limb movement data is collected at an acute stroke period. The motor activity data is transmitted to a base station. The base station is connected to one or more computers for calculating an activity value for two arms by using the limb movement data. The activity value is compared between the two arms for monitoring the motor recovery.

Still referring to FIG. 1, although the present subject matter is explained considering that the system 100 is implemented as an application on a server, it may be understood that the system 100 may also be implemented in a variety of computing systems, such as a laptop computer, a desktop computer, a notebook, a workstation, a server, a network server, and the like. In one implementation, the system 100 may be implemented in a cloud-based environment. The components and modules of the server are implemented as software and/or hardware components, such as a field programmable gate array (FPGA), an application specific integrated circuit (ASIC), and the like which performs certain tasks.

It will be understood that the system 100 may be accessed by multiple users through one or more user devices 104-1, 104-2 . . . 104-N, the user devices 104 (further referred as an electronic device) collectively referred to as user device 104 (electronic device) hereinafter, or applications residing on the user devices 104. Examples of the user devices 104 may include, but are not limited to, a portable computer, a personal digital assistant, a handheld device, and a workstation. The user devices 104 are communicatively coupled to the system 100 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

Figure 2:
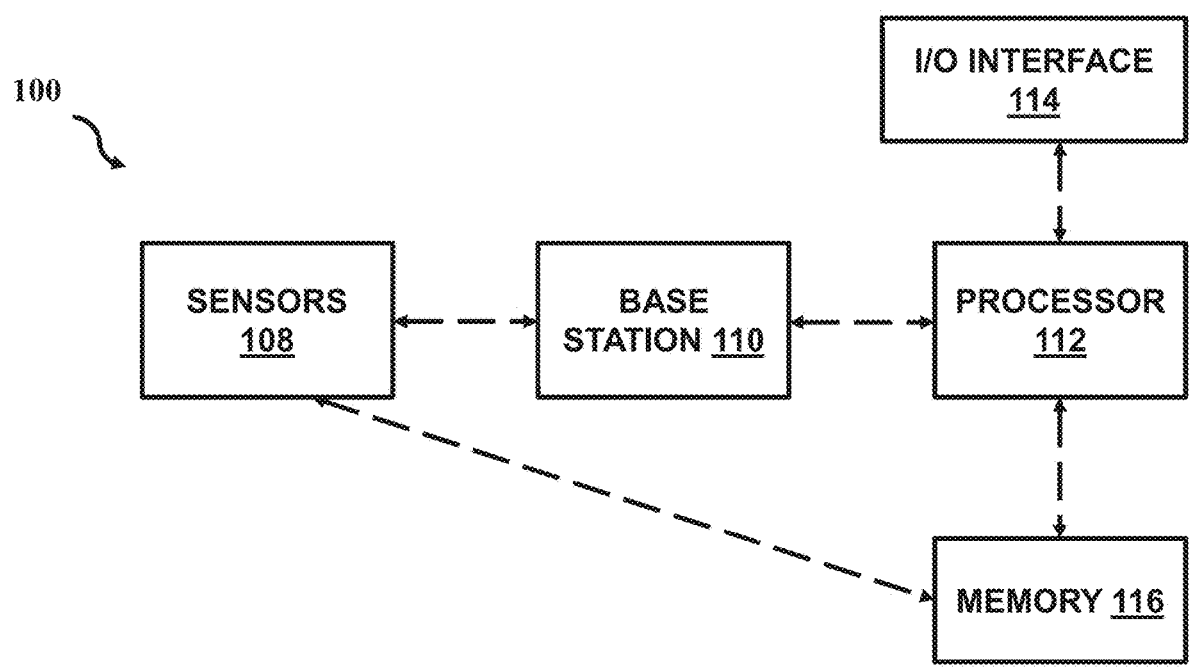
FIG. 2 illustrates a broad level architecture of the system monitoring motor recovery in the post-acute stroke treatment, in accordance with an embodiment of the present subject matter.
Figure 3A:
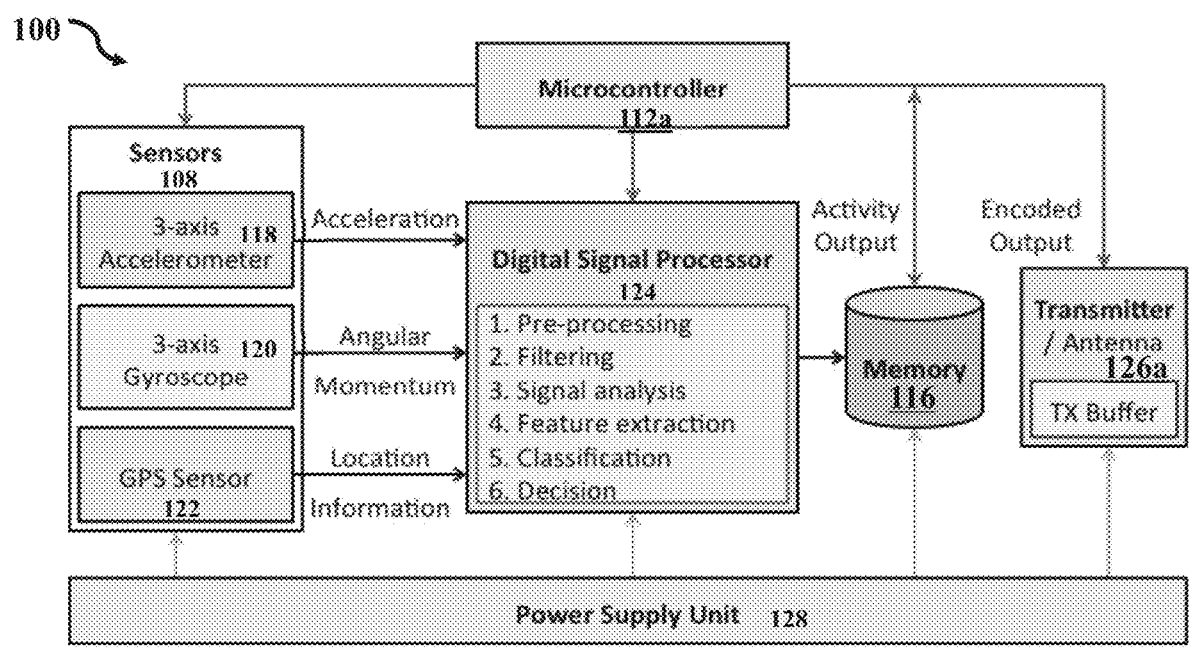
FIGS. 3a and 3b illustrates detailed components of the system monitoring motor recovery in the post-acute stroke treatment, in accordance with an embodiment of the present subject matter.
Figure 3B:
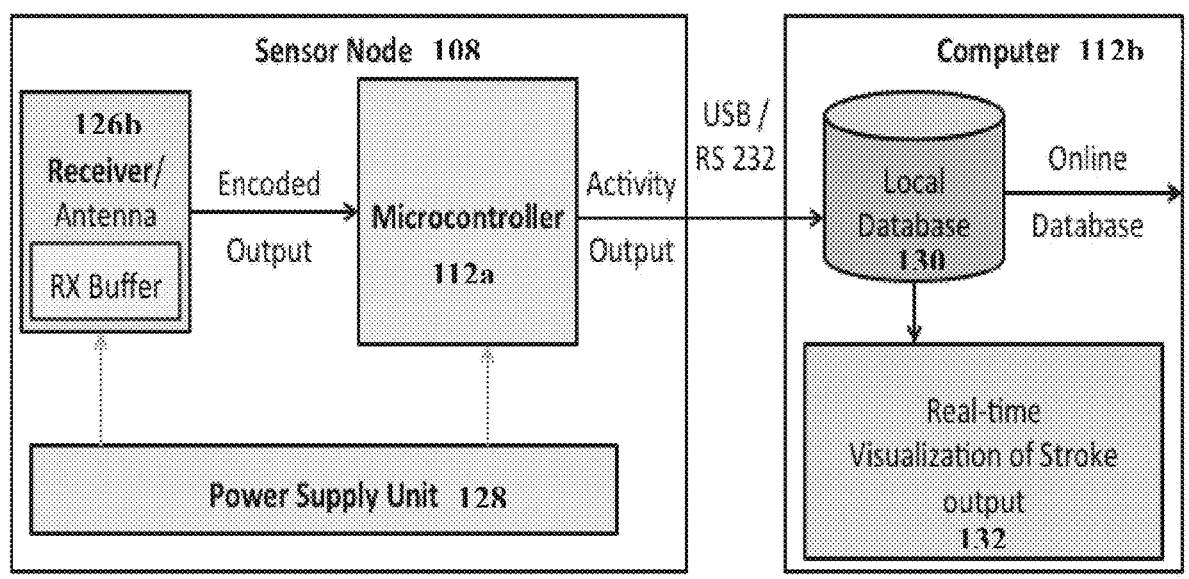

Referring now to FIG. 2 along with FIGS. 3a and 3b, the system 102 is illustrated in accordance with an embodiment of the present subject matter. In one embodiment, the system 100 comprises a sensor 108, and a base station 110. The system 100 may include at least one processor 112 (for both the sensor 108 and the base station 110), an input/output (I/O) interface 114 (herein a configurable user interface), a memory 116. The at least one processor 112 may be implemented as one or more microprocessors, microcomputers, microcontrollers, digital signal processors, central processing units, state machines, logic circuitries, and/or any devices that manipulate signals based on operational instructions. Among other capabilities, the at least one processor 112 is configured to fetch and execute computer-readable instructions stored in the memory 116.

The I/O interface 114 may include a variety of software and hardware interfaces, for example, a web interface, a graphical user interface, and the like. The I/O interface 114 may allow the system 100 to transmit and receive data and commands to or from the base station 110. Further, the I/O interface 114 may enable the system 100 to communicate with other computing devices, such as web servers and external data servers (not shown). The I/O interface 114 can facilitate multiple communications within a wide variety of networks and protocol types, including wired networks, for example, LAN, cable, etc., and wireless networks, such as WLAN, cellular, or satellite. The I/O interface 114 may include one or more ports for connecting a number of devices to one another or to another server.

The memory 116 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include modules (not shown in Figure) and may store limbs movement data in raw and filtered form in a database.

The modules (although not shown in Figure) include routines, programs, objects, components, data structures, etc., which perform particular tasks, functions or implement particular abstract data types.

In accordance with an embodiment, referring to FIG. 3a, the sensor 108 comprises a 3-axis accelerometer 118, a 3-axis Gyroscope 120, and a GPS sensor 122. The system 100 further comprises a digital signal processor 124, a transmitter (antenna or transceiver) 126a with a TX buffer and a power supply unit 128.

Referring to FIG. 3b, at the base station 110, the sensor node 108 comprises a receiver 126b with an RX buffer for encoding the limbs movement data so filtered during the sensing. The microcontroller calculates the activity and stores the activity over a computer 112b in a local database 130 for providing a real-time visualization of stroke output. The base station 110 may also comprise a transceiver for transmitting and receiving the limbs movement data and commands.

Figure 4:
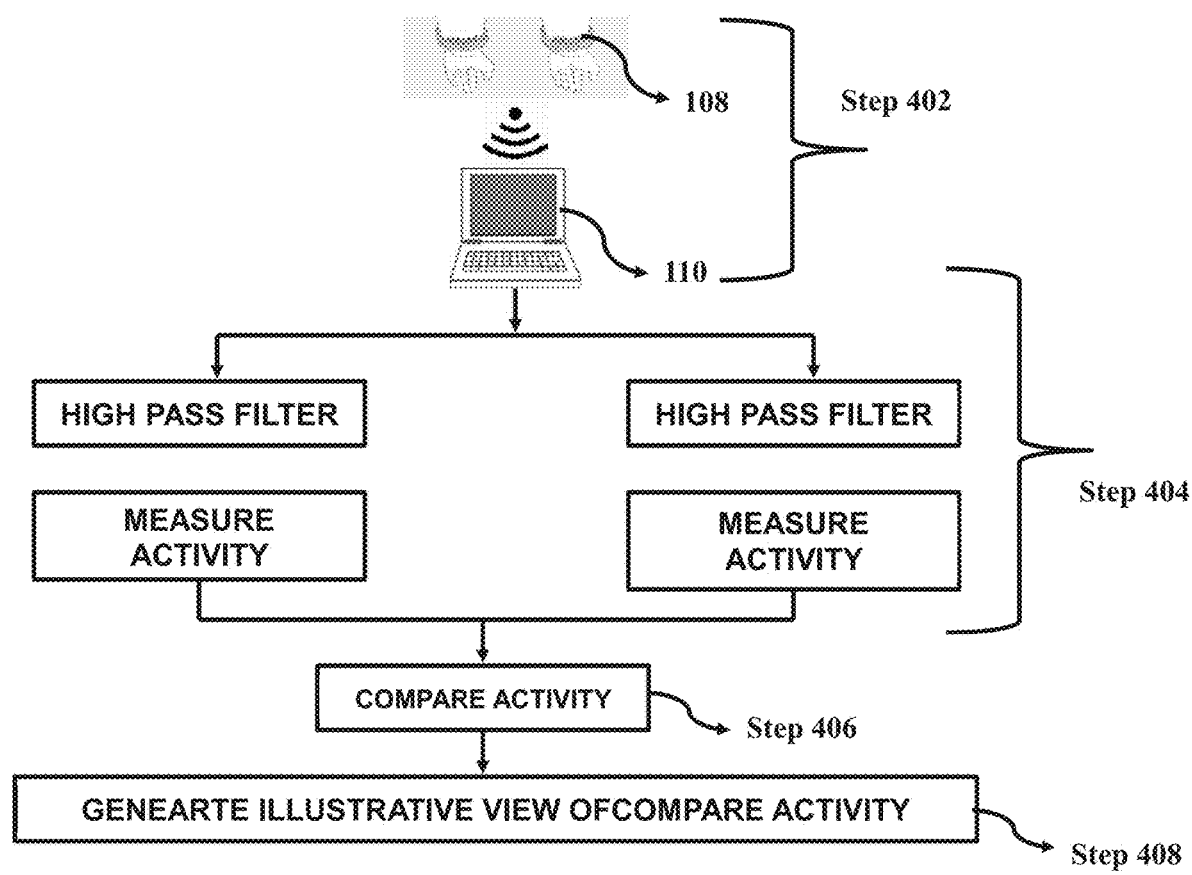
FIG. 4 shows steps involved in monitoring the motor activity in the post-acute stroke treatment, in accordance with an embodiment of the present subject matter.

Referring to FIG. 4, the at least one sensor 108 is configured to collect limbs movement data using a wireless sensor node. As shown in step 402, in one embodiment, the at least one sensor 108 with the wireless sensor node may be coupled to a wearable device and user (patient) may wear the wearable device in two arms. The at least one sensor 108 monitors the motor activity of the patient in a continuous manner. The sensor node 108 comprises the 3-dimensional accelerometer 118 sensor for measuring motion of the two arms along 3 axes. The sensor node 108 further comprises the gyroscope 120 for measuring an orientation of the two arms in real-time space. The sensor node 108 further comprises a Photoplethysmogram for measuring the heart rate and a temperature device for measuring a temperature of body of the patient.

The limbs movement data is then transmitted to a high pass filter before transmitting to the base station 110 for measuring an activity in two arms, as shown in step 404. The activity in two arms is compared in step 406 and illustrative view of the comparison of activity in the two arms is generated for use of professionals (such as doctors) in step 408. In case the base station 110 is not available, the limbs movement data is stored in a non-volatile storage memory.

Figure 5:
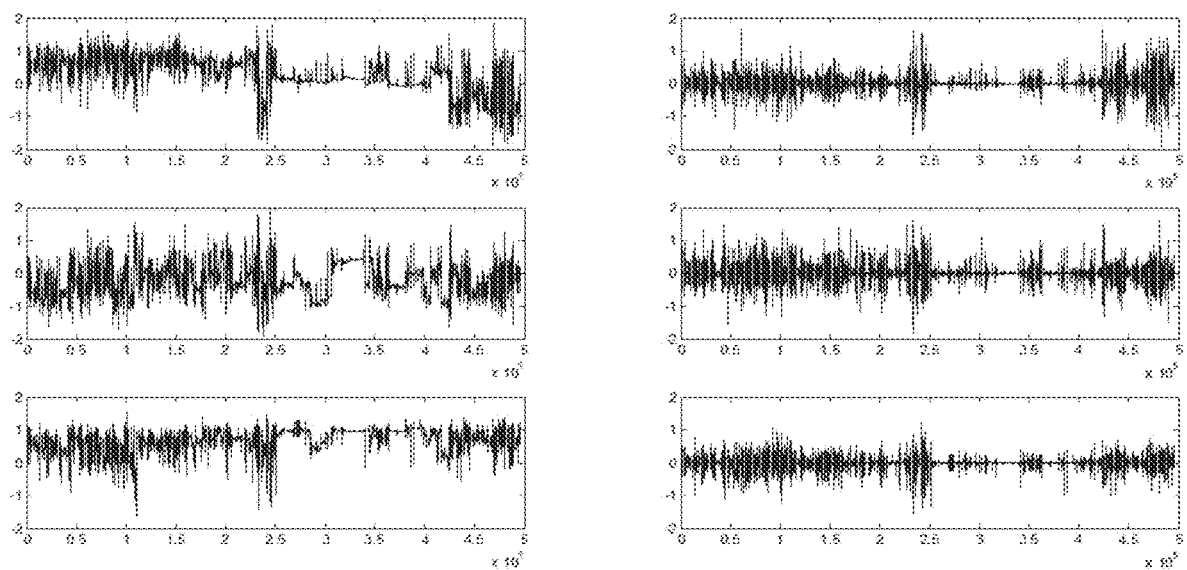
FIG. 5 shows limbs movement data in a raw form, in accordance with an embodiment of the present subject matter.

In an example embodiment, referring to FIG. 5, the limbs movement data in raw form is filtered by implementing the basic Butterworth Highpass filter in Matlab before processing for the motor recovery monitoring. The cut-off frequency is 2.5 Hz from a trial range of 1 Hz to 5 Hz while reducing a baseline drift.

In an example embodiment, the accelerometer 118 data may be collected for first four hours and another one hour after 24 hours. Observed National Institute of Health Stroke Scale (NIHSS) motor scores and observed NIHSS overall score are recorded at an onset time i.e. $0^{th}$ hour, $1^{st}$ hour, $2^{nd}$ hour $3^{rd}$ hour and 24 hours. In a scenario, if the patient enters into a hospital at 9 am, the limbs movement data is collected between 9 am and 1 pm (by recording at 9 am, 10 am, 11 am, 12 pm) on the day patient had arrived. The limbs movement data is further collected between 9 am and 10 am on a following day.

Figure 6:
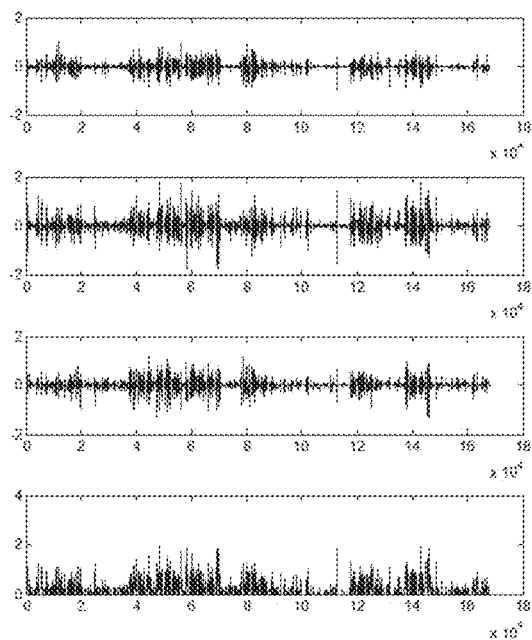
FIG. 6 shows limbs movement data to be used for calculating acceleration, in accordance with an exemplary embodiment of the present subject matter.
Figure 6:
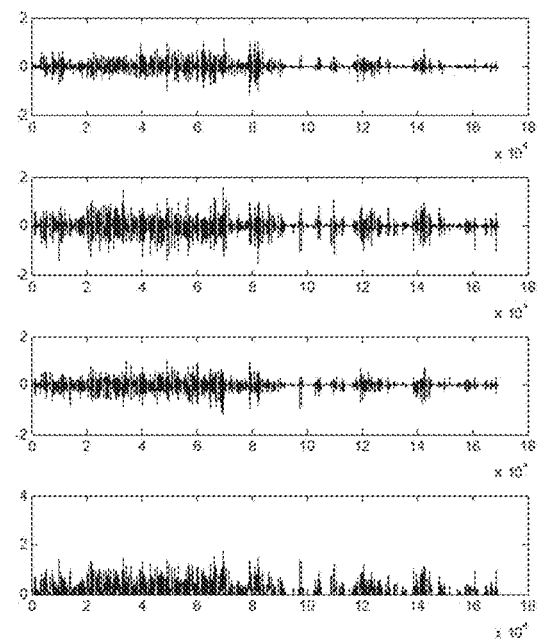

Let a sampling frequency of the limbs movement so collected is 100 Hz and let the transceiver (transmitter 126) transmits three packets of data to the base station 110 every second. Each packet out of the three packets of the limbs movement data contains several values of acceleration along x, y and z axes. FIG. 6 shows limbs movement data to be used for calculating the acceleration.

The acceleration value is determined by below mentioned formula:

$$A_L = \sqrt{a_{lx}^2 + a_{ly}^2 + a_{lz}^2}$$

Figure 7:
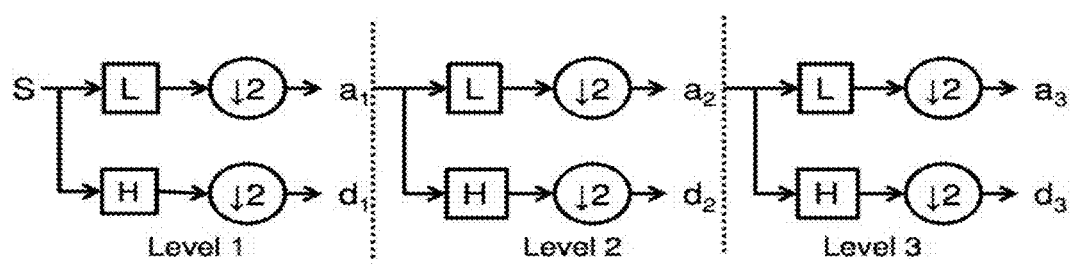
FIG. 7 provides an illustrative view of steps in obtaining a 4 level Discrete Wavelet Transform (DWT), in accordance with an exemplary embodiment of the present subject matter.

The acceleration values so calculated are further used for activity detection in the two arms (affected arm and the unaffected arm) at the base station 110. The acceleration data is divided into 10 minutes window. db3 is used for obtaining a 4 level Discrete Wavelet Transform (DWT). The detailed and approximate coefficients are used and power and Shannon entropy are calculated for the detailed and approx. coefficients. Feature vector is then obtained from the power and entropy values and is fed into a feed forward neural network classifier with 4 state outputs as shown in FIG. 7.

At the base station 110, a time stamp is generated instead of time stamp generation at a source node. The generation of the time stamp at the base station 110 avoids a time synchronization problem in wireless sensor nodes. Thus, the base station 110 receives 6 acceleration values at a particular instant.

At the sensor node 108, the limbs movement data is pre-processed by the digital signal processor 124. The digital signal processor analyses the signal in the limbs movement data and performs one or more pre-processing actions. The pre-processing actions comprises filtering, signal analysis, feature extraction, classification and decision.

At the base station 110, a compare module is configured to compare the activity between the two arms for monitoring the motor activity. The activities comprises frequency distribution of movement in each of an affected arm of the two arms and an unaffected arm of the two arms. The frequency distribution between the affected arm and the unaffected arm is compared using the limbs movement data obtained through the accelerometer sensor 118 and the gyroscope sensor 120.

Figure 8:
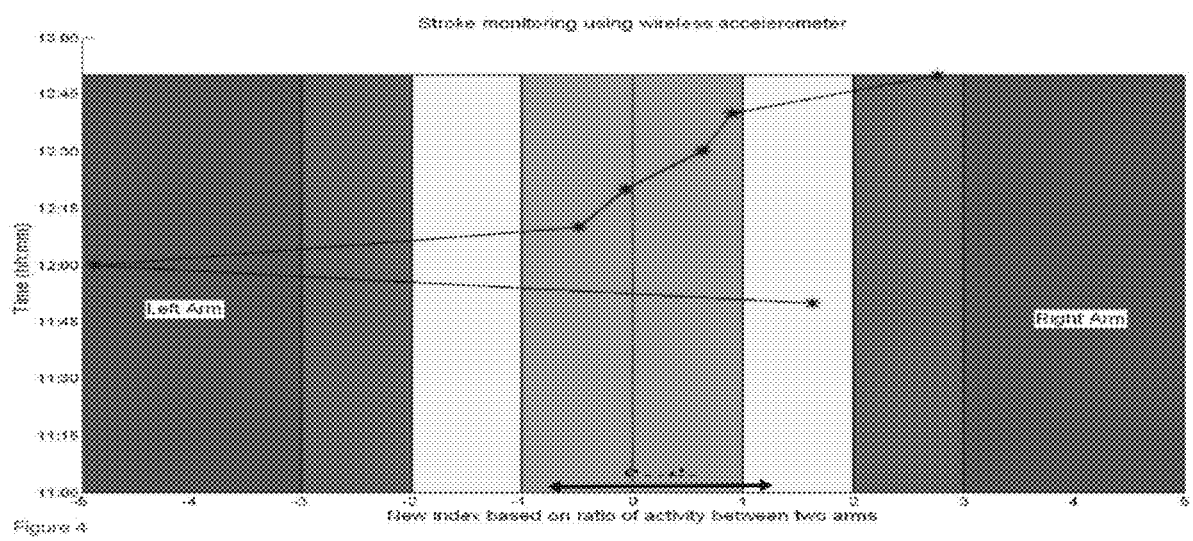
FIG. 8 provides an index based ratio of activity between two arms, in accordance with an embodiment of the present subject matter.

In FIG. 8, while calculating the comparative results between the activity data of the two arms, a 10 minute window is considered in a second stage and a cumulative integral is calculated within the window. The area under the curve is calculated every 10 minutes. The ratio of energy indicates the activity in affected arm and the activity in the unaffected arm. Using a predefined threshold value, the ratio of energies so calculated is converted into the NIHSS equivalent index.

Results of comparison between the activities of the two arms is illustrated in a visual form over a customized graphic user interface. Referring to FIG. 8, the online visualization of stroke monitoring is shown. The FIG. 8 is divided into two parts vertically along the midway. The divided parts indicate the two arms (the affected arm and the unaffected arm). In FIG. 8, section 1 represents normal activity and section 2 represents severe arm disability. In NIHSS, custom color coding is used for illustrating severity of stroke. Section 1 may be represented in green color and sections 1 may be represented in red color.

In FIG. 8, x-axis indicates stroke index and y-axis indicates a time of recording. Negative stroke index is for left hand and positive stroke index is for right hand. In case of moving away from 0 in any direction in the Figure, a severity of stroke increases. The graph shown in FIG. 8 is an online graph and the online graph gets updated every 10 minutes according to the continuous recording of the limbs movement data by the sensors to provide more accurate monitoring.

In an embodiment, the limbs movement data and the activity value so compared are stored in a cloud network in a database. By using a time-frequency algorithm, within the cloud network, a check module checks a recovery status of the patient based on the comparison of the activity. In case the activity value exceeds a predefined threshold, an alert and notification module generates a trigger and transmits a notification to external users. In an example, the notification includes a Short Message Service (SMS) and the external users comprise doctors.

This is to be noted by a person ordinarily skilled in the art that the system is developed as a model based on labels given by field experts. New labels are created when new limb movement data is received and activity levels are calculated.

Figure 9:
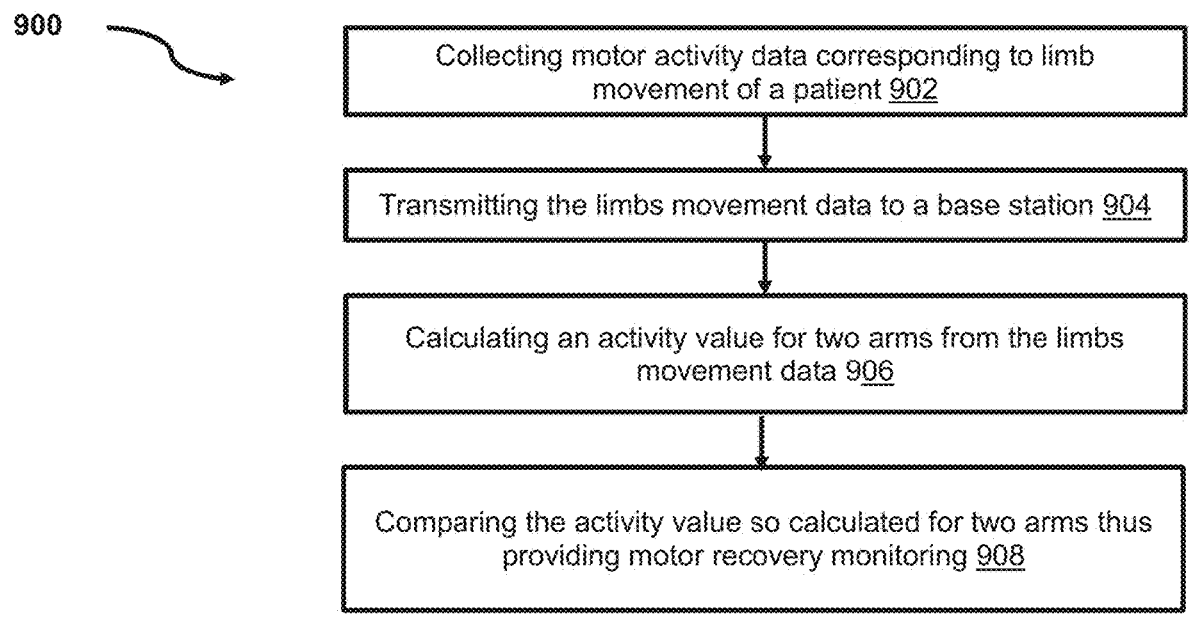
FIG. 9 provides a flow chart of a method for monitoring recovery activity in the post-stroke treatment, in accordance with an embodiment of the present subject matter.

Referring now to FIG. 9, a method 900 for motor recovery monitoring in the post-acute stroke treatment is shown, in accordance with an embodiment of the present subject matter. The method 900 may be described in the general context of computer executable instructions. Generally, computer executable instructions can include routines, programs, objects, components, data structures, procedures, modules, functions, etc., that perform particular functions or implement particular abstract data types. The method 900 may also be practiced in a distributed computing environment where functions are performed by remote processing devices that are linked through a communications network. In a distributed computing environment, computer executable instructions may be located in both local and remote computer storage media, including memory storage devices.

The order in which the method 900 is described is not intended to be construed as a limitation, and any number of the described method blocks can be combined in any order to implement the method 900 or alternate methods. Additionally, individual blocks may be deleted from the method 900 without departing from the spirit and scope of the subject matter described herein. Furthermore, the method can be implemented in any suitable hardware, software, firmware, or combination thereof. However, for ease of explanation, in the embodiments described below, the method 900 may be considered to be implemented in the above described system 100.

In FIG. 9, at block 902, motor activity data corresponding to limb movement of a patient is collected. The motor activity data (or limb movement data) is collected by at least one sensor 108.

At step 904, limb movement data is transmitted to a base station. The limb movement data is pre-processed and filtered before transmission. The limb movement data may be transmitted by a transceiver coupled to the sensor 108.

At step 906, an activity value for two arms is calculated by using the limb movement so filtered. The activity value is calculated for the affected arm and the unaffected arm.

At step 908, the activity value between the two arms is compared providing the motor recovery monitoring. The comparative analysis of the activity is illustrated in a graphical form as explained earlier and is not repeated for the sake of brevity.

Figure 10:
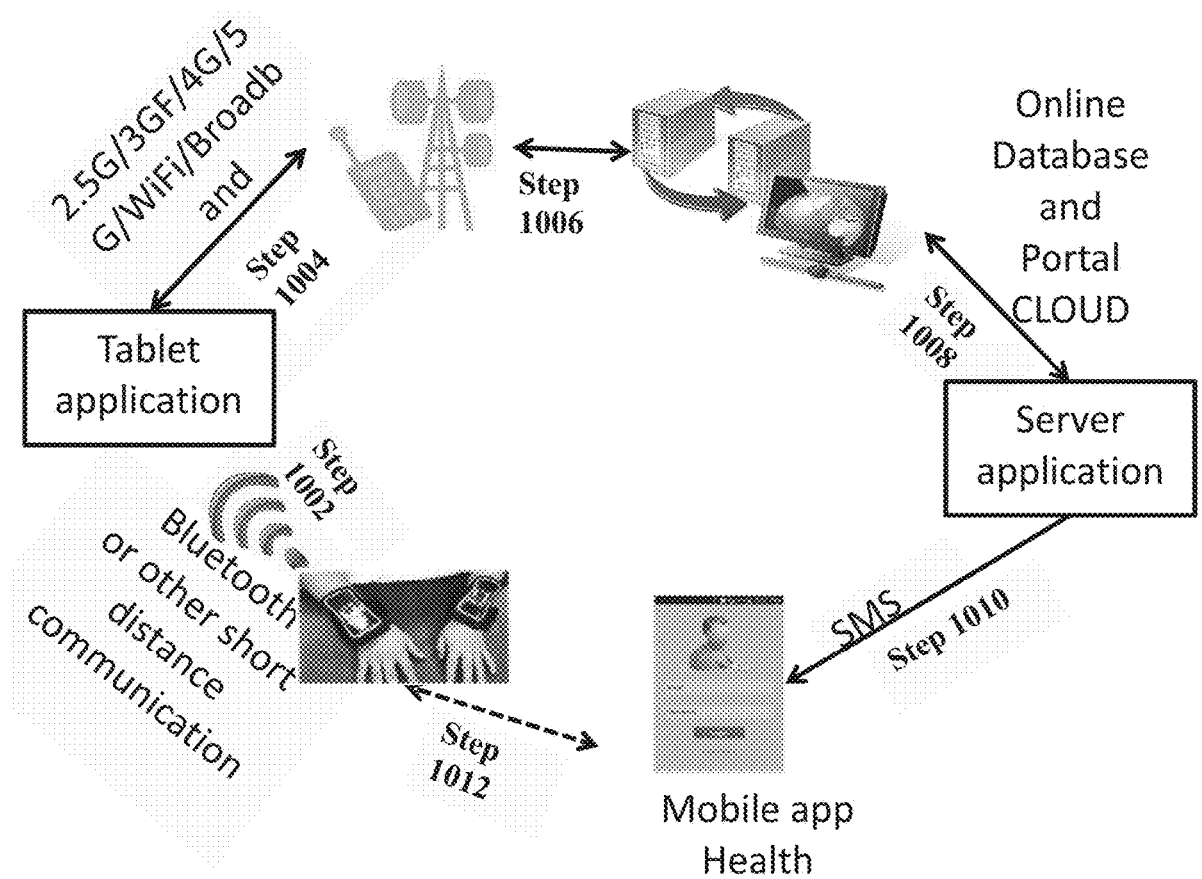
FIG. 10 provides an exemplary mechanism of monitoring motor recovery in the post-stroke treatment, in accordance with an embodiment of the present subject matter.

In accordance with an exemplary embodiment, referring to FIG. 10, a mechanism of monitoring motor activity in case of the post stroke treatment is shown. In step 1002, the sensors 108 tied to wrists of the patient senses the limb movement data and transmits the limbs movement data to an application of an electronic device (tablet application). From the electronic device the limbs movement data is shared with the base station 110 in step 1004. In step 1006, the limbs movement data may be stored with online database and portal cloud for a purpose of analysis as shown in step 1008. The analytical results of the limbs movement data may be accessed by health professionals in step 1010 so that the health professionals may sent notifications and alerts. The health professionals may also directly access the limbs movement data collected by the sensors in step 1012.

The written description describes the subject matter herein to enable any person skilled in the art to make and use the embodiments of the invention. The scope of the subject matter embodiments are defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The invention claimed is:

1. A system for monitoring motor recovery in a post-acute stroke period, the system comprising:
   at least one sensor, for collecting a motor activity of an affected and unaffected limb movement of a subject, wherein the motor activity is sensed at the post-acute stroke period;
   a first processor communicatively coupled to the at least one sensor;
   a memory unit coupled to the first processor, wherein the memory unit stores a plurality of modules to be executed by the first processor, wherein the plurality of modules are configured for:
      transmitting data associated with the motor activity data to at least one base station; and
   the at least one base station comprising:
      a receiver for receiving the motor activity data; and
      a second processor with a memory, wherein the memory stores a plurality of modules to be executed by the second processor, and wherein the plurality of modules are configured for:
         time-stamping the motor activity data from the at least one sensor;
         calculating an activity value for the affected limb and the unaffected limb from the motor activity data in a predefined time window;
         comparing the activity values for the affected limb and the unaffected limb of the subject to monitor the motor activity of the affected limb;
         displaying at least one of the motor activity data and the results of the comparison in a suitable visual form;
         storing the motor activity data and the activity values on a cloud network for performing a time-frequency analysis of the data for calculating a recovery status of the subject;
         creating one or more labels, based on received motor activity data and calculated activity values;
         applying machine learning models to the created labels for predicting motor deterioration and motor recovery;
         initiating one or more actions based on the recovery status;
         issuing an alert when the difference in the activity values exceeds a predetermined threshold; and
         sending a message to an electronic device associated with a user.

2. The system as claimed in claim 1, wherein the at least one sensor collects the motor activity at a predefined sampling rate.

3. The system as claimed in claim 1, wherein the at least one sensor comprises a 3-axis accelerometer, a gyroscope, a temperature measuring device, and a Photoplethysmogram.

4. The system as claimed in claim 1, wherein the motor activity data comprises acceleration data corresponding to affected limb and the unaffected limb of the subject.

5. The system as claimed in claim 1, comprises:
   a power supply unit for adjusting at least one of a predefined sampling rate and a communication frequency.

6. The system as claimed in claim 1, comprising:
   a non-volatile storage memory for storing the limbs movement data in case the at least one base station is not in a range.

7. The system as claimed in claim 1, comprising:
   the cloud network with a database for storing the limbs movement data.

8. The system as claimed in claim 1, comprising:
   a check module for checking the recovery status based on the comparison of the activity value; and
   an alert and notification module for sending alerts to the one or more external users in case a level of the activity exceeds a threshold value.

9. The system as claimed in claim 1, wherein the second processor of the at least one base station is configured to:
   generate stroke severity score (similar to National Institute of Health Stroke Scale (NUBS) score) based on comparison of the activity score between the affected limb and the unaffected limb of the subject.

10. A method for providing motor recovery monitoring in a post-acute stroke period, the method comprising:
    collecting, by at least one sensor, a motor activity of an affected and unaffected limbs movement of a subject, wherein the motor activity data is collected at the post-acute stroke period;
    transmitting, by the at least one sensor, data associated with the motor activity to at least one base station;
    time-stamping the motor activity data received from the at least one sensor, at the base station;
    calculating, by a processor, an activity value for the affected limb and the unaffected limb of the subject, by using the motor activity data in a predefined time window;
    comparing, by the processor, the activity values for the affected limb and the unaffected limb of the subject;
    displaying at least one of the motor activity data and the results of the comparison in a suitable visual form;
    storing the motor activity data and the activity values on the cloud for performing a time-frequency analysis of the data for calculating a recovery status of the subject, from the motor activity data from a predefined time window;

creating one or more labels, based on the received motor activity data and calculated activity values;

applying machine learning models to the created labels for predicting motor deterioration and motor recovery;

initiating one or more actions based on the recovery status;

issuing an alert when the difference in the activity values exceeds a predetermined threshold; and sending a message to an electronic device associated with a user.

11. The method as claimed in claim 10, wherein the motor activity data is collected at a predefined sampling rate.

12. The method as claimed in claim 10, wherein the motor activity data comprises acceleration data corresponding to affected limb and the unaffected limb of the subject.

13. The method as claimed in claim 10, wherein the calculating comprising:

pre-processing the activity values;

extracting one or more features from the activity values; and classifying the one or more features from the activity values.

14. The method as claimed in claim 10, wherein the activity value is calculated in the predefined time window ranging from a 5 minute time window to a 15 minute time window.

15. The method as claimed in claim 10, wherein the comparing comprises: comparing the activity value between an affected limb of the two arms and a non-affected limb based on a time synchronization.

* * * * *